(12) United States Patent
Schaer et al.

(10) Patent No.: US 7,587,247 B2
(45) Date of Patent: Sep. 8, 2009

(54) CARDIAC HARNESS HAVING AN OPTIMAL IMPEDANCE RANGE

(75) Inventors: Alan Schaer, San Jose, CA (US); Matthew G. Fishler, Sunnyvale, CA (US)

(73) Assignee: Paracor Medical, Inc., Sunnyvale, CA (US)

( * ) Notice: Subject to any disclaimer, the term of this patent is extended or adjusted under 35 U.S.C. 154(b) by 591 days.

(21) Appl. No.: 11/195,329

(22) Filed: Aug. 1, 2005

(65) Prior Publication Data

US 2007/0027516 A1    Feb. 1, 2007

(51) Int. Cl.
*A61N 1/05* (2006.01)

(52) U.S. Cl. .......................................... 607/129; 600/16

(58) Field of Classification Search .................. 607/9, 607/129–132; 600/16
See application file for complete search history.

(56) References Cited

U.S. PATENT DOCUMENTS

| | | | |
|---|---|---|---|
| 2,278,926 A | 4/1942 | Hartwell |
| 2,826,193 A | 3/1958 | Vineberg |
| 3,464,322 A | 9/1969 | Pequignot |
| 3,513,836 A | 5/1970 | Sausse |
| 3,587,567 A | 6/1971 | Schiff |
| 3,613,672 A | 10/1971 | Schiff |
| 3,966,401 A | 6/1976 | Hancock et al. |
| 3,983,863 A | 10/1976 | Janke et al. |
| 3,988,782 A | 11/1976 | Dardik et al. |
| 4,011,947 A | 3/1977 | Sawyer |
| 4,048,990 A | 9/1977 | Goetz |
| 4,065,816 A | 1/1978 | Sawyer |
| 4,108,161 A | 8/1978 | Samuels et al. |
| 4,192,293 A | 3/1980 | Asrican |
| 4,211,325 A | 7/1980 | Wright |
| 4,261,342 A | 4/1981 | Aranguren Duo |
| 4,306,318 A | 12/1981 | Mano et al. |
| 4,372,293 A | 2/1983 | Vijil-Rosales |
| 4,403,604 A | 9/1983 | Wilkinson et al. |
| 4,428,375 A | 1/1984 | Ellman |
| 4,512,471 A | 4/1985 | Kaster et al. |
| 4,536,893 A | 8/1985 | Parravicini |
| 4,545,783 A | 10/1985 | Vaughn |

(Continued)

FOREIGN PATENT DOCUMENTS

DE    3831 540 A1    4/1989

(Continued)

OTHER PUBLICATIONS

Bencini, Adriano, M.D., *The "Pneumomassage" of the Heart*, Surgery, vol. 39, No. 3, Mar. 1956.

(Continued)

*Primary Examiner*—Carl H Layno
*Assistant Examiner*—Brian T Gedeon
(74) *Attorney, Agent, or Firm*—Fulwider Patton LLP

(57) ABSTRACT

A system for treating the heart including a cardiac harness configured to conform generally to at least a portion of a patient's heart. The system also includes an electrode associated with the cardiac harness and positioned on or proximate to the epicardial surface of the heart. In order to ensure that the electrode will operate with a pulse generator, the system has an impedance between approximately 10 ohms and approximately 120 ohms.

12 Claims, 3 Drawing Sheets

U.S. PATENT DOCUMENTS

| | | | |
|---|---|---|---|
| 4,628,937 A | 12/1986 | Hess et al. | |
| 4,630,597 A | 12/1986 | Kantrowitz et al. | |
| 4,665,906 A | 5/1987 | Jervis | |
| 4,690,134 A | 9/1987 | Snyders | |
| 4,697,703 A | 10/1987 | Will | |
| 4,750,619 A | 6/1988 | Cohen et al. | |
| 4,821,723 A * | 4/1989 | Baker et al. | 607/7 |
| 4,827,932 A | 5/1989 | Ideker et al. | |
| 4,834,707 A | 5/1989 | Evans | |
| 4,838,288 A | 6/1989 | Wright et al. | |
| 4,840,626 A | 6/1989 | Linsky et al. | |
| 4,863,016 A | 9/1989 | Fong et al. | |
| 4,878,890 A | 11/1989 | Bilweis | |
| 4,936,857 A | 6/1990 | Kulik | |
| 4,957,477 A | 9/1990 | Lundbäck | |
| 4,960,424 A | 10/1990 | Grooters | |
| 4,973,300 A | 11/1990 | Wright | |
| 4,976,730 A | 12/1990 | Kwan-Gett | |
| 5,031,762 A | 7/1991 | Heacox | |
| 5,057,117 A | 10/1991 | Atweh | |
| 5,067,957 A | 11/1991 | Jervis | |
| 5,087,243 A | 2/1992 | Avitall | |
| 5,098,369 A | 3/1992 | Heilman et al. | |
| 5,106,386 A | 4/1992 | Isner et al. | |
| 5,119,804 A | 6/1992 | Anstadt | |
| 5,131,905 A | 7/1992 | Grooters | |
| 5,150,706 A | 9/1992 | Cox et al. | |
| 5,169,381 A | 12/1992 | Snyders | |
| 5,186,711 A | 2/1993 | Epstein | |
| 5,190,546 A | 3/1993 | Jervis | |
| 5,192,314 A | 3/1993 | Daskalakis | |
| 5,197,978 A | 3/1993 | Hess | |
| 5,256,132 A | 10/1993 | Snyders | |
| 5,279,539 A | 1/1994 | Bohan et al. | |
| 5,290,217 A | 3/1994 | Campos | |
| 5,336,254 A | 8/1994 | Brennen et al. | |
| 5,344,442 A | 9/1994 | Deac | |
| 5,352,184 A | 10/1994 | Goldberg et al. | |
| 5,356,432 A | 10/1994 | Rutkow et al. | |
| 5,366,460 A | 11/1994 | Eberbach | |
| 5,383,840 A | 1/1995 | Heilman et al. | |
| 5,385,156 A | 1/1995 | Oliva | |
| 5,385,229 A | 1/1995 | Bittmann et al. | |
| 5,385,528 A | 1/1995 | Wilk | |
| 5,405,360 A | 4/1995 | Tovey | |
| 5,429,584 A | 7/1995 | Chiu | |
| 5,433,727 A | 7/1995 | Sideris | |
| 5,456,711 A | 10/1995 | Hudson | |
| 5,460,962 A | 10/1995 | Kemp | |
| 5,500,015 A | 3/1996 | Deac | |
| 5,507,779 A | 4/1996 | Altman | |
| 5,509,428 A | 4/1996 | Dunlop | |
| 5,524,633 A | 6/1996 | Heaven et al. | |
| 5,533,958 A | 7/1996 | Wilk | |
| 5,534,024 A | 7/1996 | Rogers et al. | |
| 5,545,210 A | 8/1996 | Hess et al. | |
| 5,558,617 A | 9/1996 | Heilman et al. | |
| 5,571,215 A | 11/1996 | Sterman et al. | |
| 5,582,616 A | 12/1996 | Bolduc et al. | |
| 5,584,803 A | 12/1996 | Stevens et al. | |
| 5,593,424 A | 1/1997 | Northrup III | |
| 5,593,441 A | 1/1997 | Lichtenstein et al. | |
| 5,597,378 A | 1/1997 | Jervis | |
| 5,603,337 A | 2/1997 | Jarvik | |
| 5,607,477 A | 3/1997 | Schindler et al. | |
| 5,647,372 A | 7/1997 | Tovey et al. | |
| 5,647,380 A | 7/1997 | Campbell et al. | |
| 5,695,525 A | 12/1997 | Mulhauser et al. | |
| 5,702,343 A | 12/1997 | Alferness | |
| 5,713,954 A | 2/1998 | Rosenberg et al. | |
| 5,727,569 A | 3/1998 | Benetti et al. | |
| 5,749,839 A | 5/1998 | Kovacs | |
| 5,782,746 A | 7/1998 | Wright | |
| 5,800,334 A | 9/1998 | Wilk | |
| 5,800,528 A | 9/1998 | Lederman et al. | |
| 5,814,097 A | 9/1998 | Sterman et al. | |
| 5,824,028 A | 10/1998 | Knisley | |
| 5,836,311 A | 11/1998 | Borst et al. | |
| 5,848,962 A | 12/1998 | Feindt et al. | |
| 5,849,005 A | 12/1998 | Garrison et al. | |
| 5,853,422 A | 12/1998 | Huebsch et al. | |
| 5,865,791 A | 2/1999 | Whayne et al. | |
| 5,904,690 A | 5/1999 | Middleman et al. | |
| 5,910,124 A | 6/1999 | Rubin | |
| 5,927,284 A | 7/1999 | Borst et al. | |
| 5,948,019 A | 9/1999 | Shu et al. | |
| 5,957,977 A | 9/1999 | Melvin | |
| 5,961,440 A | 10/1999 | Schweich, Jr. et al. | |
| 5,976,069 A | 11/1999 | Navia et al. | |
| 5,979,456 A | 11/1999 | Magovern | |
| 5,984,857 A | 11/1999 | Buck et al. | |
| 5,990,378 A | 11/1999 | Ellis | |
| 6,007,486 A | 12/1999 | Hunt et al. | |
| 6,015,378 A | 1/2000 | Borst et al. | |
| 6,024,096 A | 2/2000 | Buckberg | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,071,303 A | 6/2000 | Laufer | |
| 6,076,013 A | 6/2000 | Brennan et al. | |
| 6,077,214 A | 6/2000 | Mortier et al. | |
| 6,077,218 A | 6/2000 | Alferness | |
| 6,079,414 A | 6/2000 | Roth | |
| 6,085,754 A | 7/2000 | Alferness et al. | |
| 6,095,968 A | 8/2000 | Snyders | |
| 6,110,100 A | 8/2000 | Talpade | |
| 6,117,159 A | 9/2000 | Huebsch et al. | |
| 6,117,979 A | 9/2000 | Hendriks et al. | |
| 6,123,662 A | 9/2000 | Alferness et al. | |
| 6,125,852 A | 10/2000 | Stevens et al. | |
| 6,126,590 A | 10/2000 | Alferness | |
| 6,155,968 A | 12/2000 | Wilk | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |
| 6,165,120 A | 12/2000 | Schweich, Jr. et al. | |
| 6,165,121 A | 12/2000 | Alferness | |
| 6,165,122 A | 12/2000 | Alferness | |
| 6,166,184 A | 12/2000 | Hendriks et al. | |
| 6,169,922 B1 | 1/2001 | Alferness et al. | |
| 6,174,279 B1 | 1/2001 | Girard | |
| 6,179,791 B1 | 1/2001 | Krueger | |
| 6,183,411 B1 | 2/2001 | Mortier et al. | |
| 6,190,408 B1 | 2/2001 | Melvin | |
| 6,193,648 B1 | 2/2001 | Krueger | |
| 6,206,820 B1 | 3/2001 | Kazi et al. | |
| 6,214,047 B1 | 4/2001 | Melvin | |
| 6,221,103 B1 | 4/2001 | Melvin | |
| 6,224,540 B1 | 5/2001 | Ledermann et al. | |
| 6,230,714 B1 | 5/2001 | Alferness et al. | |
| 6,260,552 B1 | 7/2001 | Mortier et al. | |
| 6,261,222 B1 | 7/2001 | Schweich, Jr. et al. | |
| 6,264,602 B1 | 7/2001 | Mortier et al. | |
| 6,282,445 B1 | 8/2001 | Reinhardt et al. | |
| 6,287,250 B1 | 9/2001 | Peng et al. | |
| 6,293,906 B1 | 9/2001 | Vanden Hoek et al. | |
| 6,306,141 B1 | 10/2001 | Jervis | |
| 6,360,749 B1 | 3/2002 | Jayaraman | |
| 6,375,608 B1 | 4/2002 | Alferness | |
| 6,390,976 B1 | 5/2002 | Spence et al. | |
| 6,402,679 B1 | 6/2002 | Mortier et al. | |
| 6,402,680 B2 | 6/2002 | Mortier et al. | |
| 6,406,420 B1 | 6/2002 | McCarthy et al. | |
| 6,409,760 B1 | 6/2002 | Melvin | |

| | | |
|---|---|---|
| 6,416,459 B1 | 7/2002 | Haindl |
| 6,425,856 B1 | 7/2002 | Shapland et al. |
| 6,432,039 B1 | 8/2002 | Wardle |
| 6,451,025 B1 | 9/2002 | Jervis |
| 6,482,146 B1 | 11/2002 | Alferness et al. |
| 6,517,570 B1 | 2/2003 | Lau et al. |
| 6,537,203 B1 | 3/2003 | Alferness et al. |
| 6,544,168 B2 | 4/2003 | Alferness |
| 6,547,821 B1 | 4/2003 | Taylor et al. |
| 6,564,094 B2 | 5/2003 | Alferness et al. |
| 6,567,699 B2 * | 5/2003 | Alferness et al. ............... 607/5 |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,582,355 B2 | 6/2003 | Alferness et al. |
| 6,587,734 B2 | 7/2003 | Okuzumi |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,620 B2 | 2/2004 | Gifford, III et al. |
| 6,685,627 B2 | 2/2004 | Jayaraman |
| 6,689,048 B2 | 2/2004 | Vanden Hoek et al. |
| 6,695,769 B2 | 2/2004 | French et al. |
| 6,701,929 B2 | 3/2004 | Hussein |
| 6,702,732 B1 | 3/2004 | Lau et al. |
| 6,723,041 B2 | 4/2004 | Lau et al. |
| 6,730,016 B1 | 5/2004 | Walsh et al. |
| 6,755,779 B2 | 6/2004 | Vanden Hoek et al. |
| 6,876,887 B2 | 4/2005 | Okuzumi |
| 6,881,185 B2 | 4/2005 | Vanden Hock et al. |
| 6,887,192 B1 | 5/2005 | Whayne et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 7,155,295 B2 * | 12/2006 | Lau et al. ..................... 607/129 |
| 2001/0029314 A1 | 10/2001 | Alferness et al. |
| 2001/0047122 A1 | 11/2001 | Vanden Hoek et al. |
| 2002/0007216 A1 | 1/2002 | Melvin |
| 2002/0022880 A1 | 2/2002 | Melvin |
| 2002/0068849 A1 | 6/2002 | Schweich, Jr. et al. |
| 2002/0077524 A1 | 6/2002 | Schweich, Jr. et al. |
| 2002/0082647 A1 | 6/2002 | Alferness et al. |
| 2002/0091296 A1 | 7/2002 | Alferness |
| 2002/0103511 A1 | 8/2002 | Alferness et al. |
| 2003/0004547 A1 | 1/2003 | Owen et al. |
| 2003/0060674 A1 | 3/2003 | Gifford, III et al. |
| 2003/0060677 A1 | 3/2003 | French et al. |
| 2003/0060895 A1 | 3/2003 | French et al. |
| 2003/0199733 A1 | 10/2003 | Shapland et al. |
| 2003/0199955 A1 | 10/2003 | Struble et al. |
| 2003/0229265 A1 | 12/2003 | Girard et al. |
| 2004/0133069 A1 | 7/2004 | Shapland et al. |
| 2004/0171907 A1 | 9/2004 | Alferness et al. |
| 2004/0171908 A1 | 9/2004 | Alferness et al. |
| 2005/0059854 A1 | 3/2005 | Hoek et al. |
| 2005/0085688 A1 | 4/2005 | Girard et al. |
| 2005/0137673 A1 | 6/2005 | Lau et al. |

FOREIGN PATENT DOCUMENTS

| | | |
|---|---|---|
| DE | 38 31 540 C2 | 6/1993 |
| DE | 295 17 393 U1 | 3/1996 |
| EP | 0 370 931 A1 | 5/1990 |
| EP | 0 280 564 B1 | 6/1993 |
| EP | 0 583 012 B1 | 7/1996 |
| EP | 0 791 330 A3 | 8/1997 |
| EP | 0 919 193 A1 | 6/1999 |
| FR | 2 527 435 | 12/1983 |
| FR | 2 645 739 | 10/1990 |
| GB | 2 115 287 A | 9/1983 |
| GB | 2 209 678 A | 5/1989 |
| JP | 60-203250 | 10/1985 |
| JP | 1-145066 | 6/1989 |
| JP | 1-271829 | 10/1989 |
| SU | 1009457 | 4/1983 |
| SU | 1734767 A1 | 5/1992 |
| WO | WO 91/19465 | 12/1991 |
| WO | WO 95/06447 | 3/1995 |
| WO | WO 96/04852 | 2/1996 |
| WO | WO 96/40356 | 12/1996 |
| WO | WO 97/20505 | 6/1997 |
| WO | WO 97/24101 | 7/1997 |
| WO | WO 98/03213 | 1/1998 |
| WO | WO 98/14136 | 4/1998 |
| WO | WO 98/26738 | 6/1998 |
| WO | WO 98/29041 | 7/1998 |
| WO | WO 98/58598 | 12/1998 |
| WO | WO 00/02500 | 1/1999 |
| WO | WO 99/11201 | 3/1999 |
| WO | WO 99/30647 | 6/1999 |
| WO | WO 99/44534 | 9/1999 |
| WO | WO 99/44680 | 9/1999 |
| WO | WO 99/53977 | 10/1999 |
| WO | WO 99/56655 | 11/1999 |
| WO | WO 00/06026 | 2/2000 |
| WO | WO 00/06027 | 2/2000 |
| WO | WO 00/06028 | 2/2000 |
| WO | WO 00/13722 | 3/2000 |
| WO | WO 00/16700 | 3/2000 |
| WO | WO 00/18320 | 4/2000 |
| WO | WO 00/28912 | 5/2000 |
| WO | WO 00/28918 | 5/2000 |
| WO | WO 00/36995 | 6/2000 |
| WO | WO 00/42919 | 7/2000 |
| WO | WO 00/45735 | 8/2000 |
| WO | WO 00/48795 | 8/2000 |
| WO | WO 00/62727 | 10/2000 |
| WO | WO 00/74769 | 12/2000 |
| WO | WO 01/17437 | 3/2001 |
| WO | WO 01/21098 | 3/2001 |
| WO | WO 01/50981 | 7/2001 |
| WO | WO 01/67985 | 9/2001 |
| WO | WO 01/85061 | 11/2001 |
| WO | WO 01/91667 | 12/2001 |
| WO | WO 01/95830 | 12/2001 |
| WO | WO 01/95831 | 12/2001 |
| WO | WO 01/95832 | 12/2001 |
| WO | WO 02/13726 | 2/2002 |
| WO | WO 02/19917 | 3/2002 |
| WO | WO 03/026483 | 4/2003 |
| WO | WO 03/026484 | 4/2003 |
| WO | WO 03/026485 | 4/2003 |

OTHER PUBLICATIONS

Anstadt, George L., et al., *A New Instrument for Prolonged Mechanical Cardiac Massage, Abstracts of the 38th Scientific Sessions*, Supplement II to *Circulation*, vols. 31 and 32, pp. 375-384, Oct. 1965.

Lev, Maurice, M.D. et al., *Single (Primitive), Ventricle Circulation*, vol. 39, pp. 577-591.

Paling, D.F., *Warp Knitting Technology*, 1970.

Edie, Richard N., M.D. et al., *Surgical Repair of Single Ventricle, The Journal of Thoracic and Cardiovascular Surgery*, vol. 66, No. 3, pp. 350-360, Sep. 1972.

McGoon, Dwight C., M.D., et al., *Correction of the Univentricular Heart Having Two Atriovantricular Valves*, The Journal of Thoracic and Cardiovascular Surgery, vol. 74, No. 2, pp. 218-226, Aug. 1977.

Doty, Donald B., et al., *Septation of the Univentricular Heart: Transatrial Approach*, The Journal of Thoracic and Cardiovascular Surgery, vol. 78, No. 3, pp. 424-430, Sep. 1979.

Schetky, L. McDonald, *Shap- Memory Alloys*, Scientific American, vol. 241, No. 5, pp. 74-82, Nov. 1979.

Melton, K.N., et al., *Alloys With Two-Shape Memory Effect*, Mechanical Engineering, pp. 42-43, Mar. 1980.

Feldt, Robert H., M.D., et al., *Current Status of the Septation Procedure for Univentricular Heart*, The Journal of Thoracic and Cardiovascular Surgery, vol. 82, No. 1, pp. 93-97, Jul. 1981.

Carpentier, A., et al., *Myocardial Substitution With Stimulated Skeletal Muscle: First Successful Clinical Case*, The Lancet, Jun. 1, 1985.

Anstadt, George L. et al., *Direct Mechanical Ventricular Actuation: A Review*, Resuscitation, pp. 7-23, 1991.

Anstadt, Mark P., M.D., et al., *Pulsatile Reperfusion After Cardiac Arrest Improves Neurologic Outcome*, American Surgery, vol. 214, No. 4, pp. 478-490, Oct. 1991.

Schumacker, Harris B., Jr., *Chapter 21: Cardiac Aneurysms*, The Evolution of Cardiac Surgery, pp. 159-165, 1992.

Savage, Edward B., M.D., et al., *Repair of Left Ventricular Aneurysm*, The Journal of Thoracic and Cardiovascular Surgery, vol. 104, No. 3, pp. 752-762, Sep. 1992.

Carpentier, Alain, M.D., Ph.D., et al., *Dynamic Cardiomyoplasty at Seven Years*, The Journal of Thoracic and Cardiovascular Surgery, vol. 106, No. 1, pp. 42-54, Jul. 1993.

Capouya, Eli R., M.D., et al., *Girdling Effect of Nonstimulated Cardiomyoplasty on Left Ventricular Function*, Annals of Thoracic Surgeons, vol. 56, pp. 867-71, 1993.

Chekanov, Valeri, M.D., Ph.D., *Nonstimulated Cardiomyoplasty Wrap Attenuated the Degree of Left Ventricular Enlargement*, Annals of Thoracic Surgeons, vol. 57, pp. 1684-1690, 1997.

Chiu, Ray C.-J, *Using Skeletal Muscle for Cardiac Assistance*, Scientific American, pp. 68-77, Nov. Dec. 1994.

Kass, David A., M.D., et al., *Reverse Remodeling From Cardiomyoplasty in Human Heart Failure: External Constraint Versus Active Assist*, Circulation, vol. 91, No. 9, pp. 2314-2318, May 1, 1995.

Vaynblat, Mikhail, M.D., et al., *Cardiac Binding in Experimental Heart Failure*, Annals of Thoracic Surgery (Abstract), Supplement to Circulation, vol. 92, Suppl. 1, 1995.

Levin, Howard R., M.D., et al., *Reversal of Chronic Ventricular Dilation in Patients with End-Stage Cardiomyopathy by Prolonged Mechanical Unloading*, Circulation, vol. 91, No. 11, pp. 2717-2720, 1995.

Chaudhry, Pervaiz A., M.D., et al., *Acute Ventricular Reduction with Acorn's Cardiac Support Device Prevents Progressive Left Ventricular Dysfunction and Remodeling in Dogs with Advanced Heart Failure*, Cardiothoracic Surgery, pp. 146-148, 1996.

Oh, Joong Hwan, M.D., et al., *Mechanisms of Dynamic Cardiomyoplasty: Current Concepts*, Journal of Cardiac Surgery, vol. 11, pp. 194-199, 1996.

Badhwar, Vinay, *Power Generation From Four Skeletal Muscle Configurations Design Implications for a Muscle Powered Cardiac Assist Device*, ASAIO Journal, vol. 43, pp. M651-M657, 1997.

Westaby, Stephen, et al., *Landmarks in Cardiac Surgery*, pp. 198-199, 1997.

Cox, James L., *Left Ventricular Aneurysms: Pathophysiologic Observations and Standard Resection*, Seminars in Thoracic and Cardiovascular Surgery, vol. 9, No. 2, pp. 113-122, Apr. 1997.

Coletta, C., et al., *Prognostic Value of Left Ventricular Volume Response During Dobutamine Stress Echocardiography*, European Heart Journal, vol. 18, pp. 1599-1603, Oct. 1997.

Capomolla, Soccorso, M.D., et al., *Dobutamine and Nitroprusside Infusion in Patients With Severe Congestive Heart Failure: Hemodynamic Improvement by Discordant Effects on Mitral Regurgitation, Left Atrial Function, and Ventricular Function*, American Heart Journal, 1089-1098, Dec. 1997.

Oh, Joong Hwan, *The Effects of Prosthetic Cardiac Binding and Adynamic Cardiomyoplasty in a Model of Dilated Cardiomyopathy*, The Journal Of Thoracic and Cardiovascular Surgery, vol. 116, No. 1, pp. 148-153, 1998.

Cohn, Jay N., M.D., *Preventing Congestive Heart Failure*, American Family Physician, 6 pages, Apr. 15, 1998.

Cohn, Jay N., M.D., *Structural Basis for Heart Failure: Ventricular Remodeling and Its Pharmacological Inhibition*, Circulation, vol. 91, No. 10, pp. 2504-2507, May 15, 1995.

Gaudron, Peter, M.D., et al., *Progressive Left Ventricular Dysfunction and Remodeling After Myocardial Infarction*, Circulation, vol. 87, pp. 755-763, Mar. 1993.

Pfeiffer, Marc A., M.D., et al., *Ventricular Remodeling After Myocardial Infarction: Experimental Observations and Clinical Implications*, Circulation, vol. 81, No. 4, pp. 1161-1172, Apr. 1990.

Guasp, Francisco Torrent, *Una protesis contentiva para el tratamiento de le microcardiopatia dilatads*, Revista Española de Cardiologia, vol. 51, No. 7, Jul. 1998.

Power, J.M., et al., *Passive Ventricular Constraint Amends the Course of Heart Failure: A Study in an Ovine Model of Dilated Cardiomyopathy*, Cardiovascular Research, vol. 44, pp. 549-555, 1999.

Frazier, O.H., M.D., et al., *Left Ventricular Assist as a Bridge to Myocardial Recovery*, Annals of Thoracic Surgery, vol. 68, pp. 734-741, 1999.

Melvin, David B., *Ventricular Radius Reduction Without Resection: A Computational Analysis*, ASAIO Journal, pp. 160-165, 1999.

*Abstracts—Heart Failure*, JACC Feb. 1999.

Raman, Jai S., Fracs, et al., *Ventricular Containment as an Adjunctive Procedure in Ischemic Cardiomyopathy: Early Results*, Annals of Thoracic Surgery, vol. 70, pp. 1124-1126, Jan. 2000.

McCarthy, Patrick M., et al., *Device Based Left Ventricular Shape Change Immediately Reduces Left Ventricular Volume and Increases Ejection Fraction in a Pacing Induced Cardiomyopathy Model in Dogs*, JACC, Feb. 2000.

Chaudhry, Pervaiz A., M.D., et al., *Passive Epicardial Containment Prevents Ventricular Remodeling in Heart Failure*, Annals of Thoracic Surgeons, vol. 70, pp. 1275-1280, 2000.

Acorn Cardiovascular, Inc., *CSD Specifications Acorn Cardiac Support Device*, 2000.

*Heart "jacket" could help stop heart failure progression*, Clinicia, No. 916, Jul. 2000.

Acorn Cardiovascular, Inc., *CorCap™ Cardiac Support Device Pamphlet*, Jun. 2001.

*Medtronic's InSync Cardiac Resynchronization Therapy Device Approved by FDA*, (Press Release) Aug. 28, 2001.

Oz, Mehmet C., M.D., *Passive Ventricular Constraint for the Treatment of Congestive Heart Failure*, Annals of Thoracic Surgery, vol. 71, pp. 5185-5187, 2001.

Abstract Supplement, European Heart Journal, vol. 22, Sep. 2001.

Gorman, J., *Self-Sutures: New Material Knots Up On Its Own*, Science News, vol. 161, p. 262, Apr. 27, 2002.

Teckell-Taylor, Leah A., et al., *Passive Ventricular Restraint With Nitinol Mesh Attenuates Remodeling Following Acute Myocardial Infarction*, Abstract, American College of Cardiology (Undated).

Mann, Douglas L., M.D., *Basic Mechanisms of Remodeling and Reverse Remodeling*, presented at 6th Annual Scientific Meeting of the Heart Failure Society of America, Sep. 24, 2002.

Bocchi, Edimar a., M.D., *Arrhythmias and Sudden Death After Dynamic Cardiomyoplasty*, Circulation, vol. 90, No. 5, Part 2, pp. II-107 thru II-111, Nov. 1994.

Chachques, Juan C., M.D., *Study of Muscular and Ventricular Function in Dynamic Cardiomyoplasty: A Ten-Year Follow-Up*, The Journal of Heart and Lung Transplantation, vol. 16, No. 8, pp. 854-868, Aug. 1997.

Dullum, Mercedes K.C., M.D., et al., *Less Invasive Surgical Management of Heart Failure by Cardiac Support Device Implantation on the Beating Heart*. The Heart Surgery Forum, #2001-1818, pp. 361-363, Jan. 4-7, 2001.

Macris, Michael P. M.D., et al., *Minimally Invasive Access of the Normal Preicardium: Initial Clinical Experience with a Novel Device*, Clinical Cardiology, vol. 22 (Suppl. I), pp. I-36 thru I-39, 1999.

Thakur, Ranjan K., M.D., et al., *Latissimus Dorsi Dynamic Cardiomyoplasty: Role of Combined ICD Implantation*, Journal of Cardiac Surgery, vol. 10, pp. 295-297, 1995.

Wharton, J. Marcus, et al., *Electrophysiological Effects of Monophasic and Biphasic Stimuli in Normal and Infarcted Dogs*, PACE, vol. 13, pp. 1158-1172, Sep. 1990.

Shabetai, Ralph, *The Role of the Pericardium in the Pathophysiology of Heart Failure*, Congestive Heart Failure, Second Edition, Chapter 9, pp. 157-187, 2000.

Cohn, Jay N., M.D., *The Management of Chronic Heart Failure*, The New England Journal of Medicine, vol. 335, No. 7, pp. 490-498, Aug. 15, 1996.

Zhou, Xiaohong, et al., *Epicardial Mapping of Ventricular Defibrillation With Monophasic and Biphasic Shocks in Dogs*, Circulation Research, vol. 72, No. 1, pp. 145-160, Jan. 1993.

Shorofsky, Stephen R., et al., *Comparison of Step-Down and Binary Search Algorithms for Determination of Defibrillation Threshold in Humans*, PACE, vol. 27, pp. 218-220, Feb. 2004.

Gold, Michael R., M.D., et al., *Comparison of Single- and Dual-Coil Active Pectoral Defibrillation Lead Systems*, Journal of the American College of Cardiology vol. 31, No. 6, pp. 1391-1394, May. 1998.

Rinaldi, C. Aldo, *A Randomized Prospective Study of Single Coil Versus Dual Coil Defibrillation in Patients With Ventricular Arrhythmias Undergoing Implantable Cardioverter Defibrillator Therapy*, PACE, vol. 26, pp. 1684 1690, Aug. 2003.

Schwartzman, David, M.D., et al., *Serial Defibrillation Lead Impedance in Patients with Epicardial and Nonthoracotomy Lead Systems*, Journal of Cardiovascular Electrophysiology, vol. 7, No. 8, pp. 697-703, Aug. 1996.

Sandstedt, Bengt, et al., *Bidirectioinal Defibrillation Using Implantable Defibrillators: A Prospective Randomized Comparison Between Pectoral and Abdominal Active Generators*, PACE, vol. 24, Part I, pp. 1343-1353, Sep. 2001.

Schulte, B., et al., *Dual-Coil vs. Single-Coil Active Pectoral Implantable Difibrillator Lead Systems: Defibrillation Lead Requirements and Probability of Defibrillation Success at Multiples of the Defibrillation Engery Requirements*, Europace, vol. 3, pp. 177-180, Jul. 2001.

Application for U.S. Letters U.S. Appl. No. 09/952,145, filed Sep. 10, 2001 published on Feb. 14, 2003 as Pub. No. 02-0019580-A 1; Inventors: Lau et al.

Application for U.S. Letters U.S. Appl. No. 10/314,696, filed Dec. 9, 2002 published on Apr. 3, 2003 as Pub. No. 03-0065248-A 1; Inventors: Lau et al.

Provisional U.S. Appl. No. 60/486,062, filed Jul. 10, 2003; Inventors: Hong et al.

Application for U.S. Letters U.S. Appl. No. 10/698,237, filed Oct. 31, 2003 published on Jul. 29, 2004 as Pub. No. 04-0147805-A 1; Inventor: Lau.

Application for U.S. Letters U.S. Appl. No. 10/704,376, filed Nov. 7, 2003; Inventor: Lau.

Application for U.S. Letters U.S. Appl. No. 10/715,150, filed Nov. 17, 2003 published on Mar. 10, 2005 as Pub. No. 05-0055032; Inventor: Lau.

Provisional U.S. Appl. No. 60/535,888, filed Jan. 12, 2004; Inventors: Fishler et al.

* cited by examiner

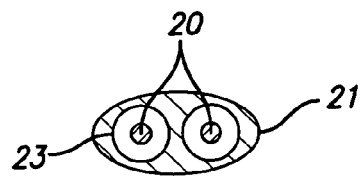
FIG. 2
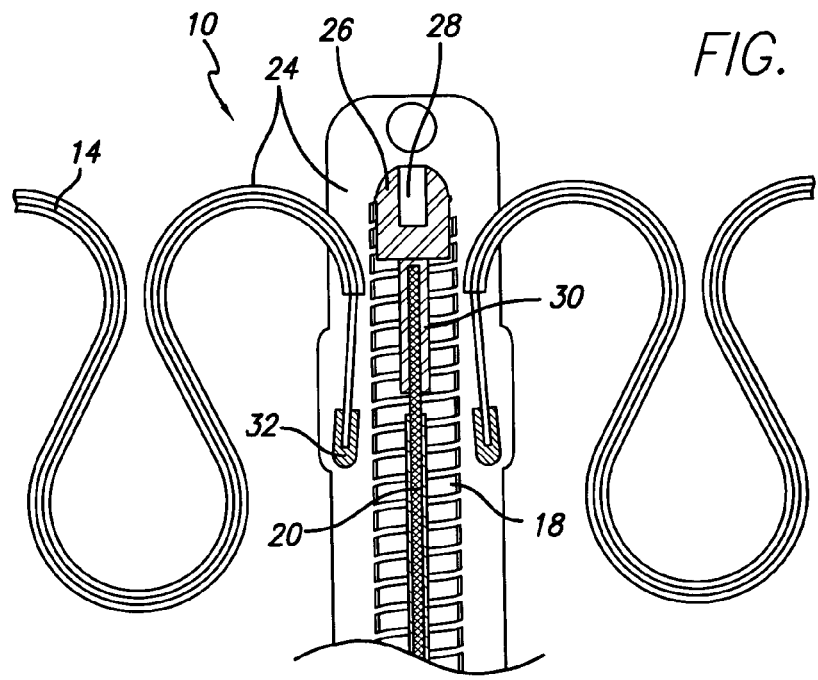
FIG. 3
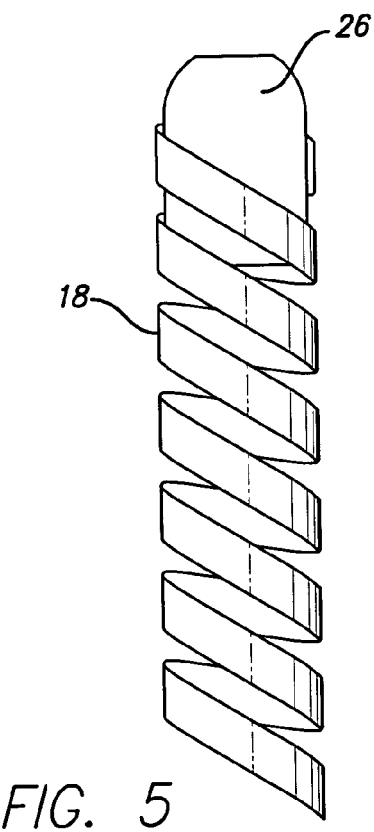
FIG. 4
FIG. 5

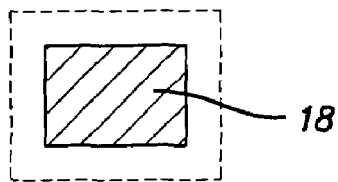
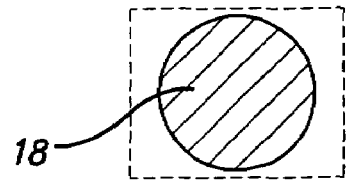
FIG. 6a   FIG. 6b
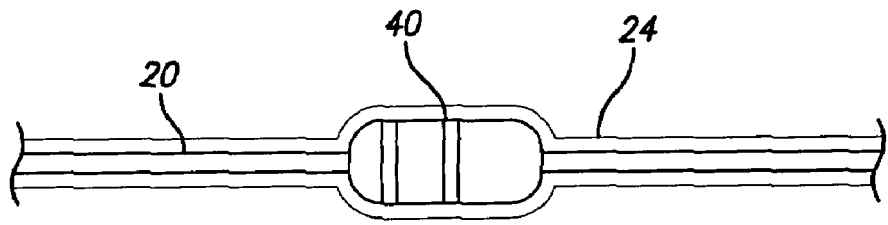
FIG. 7
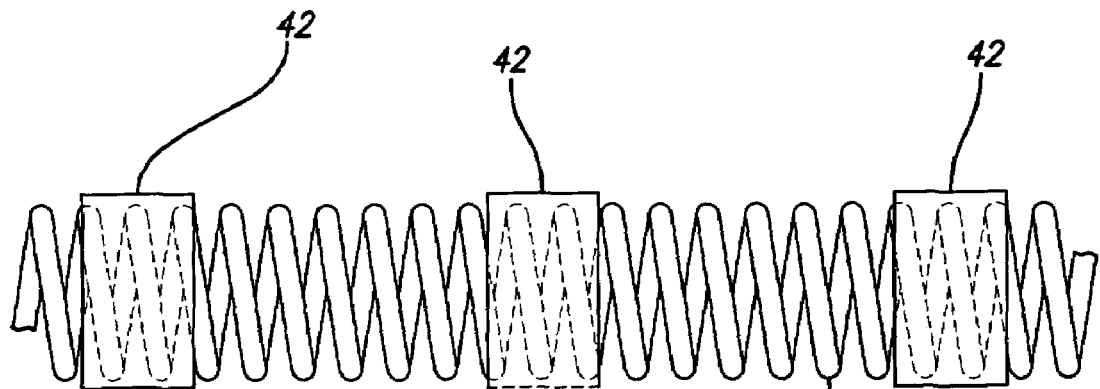
FIG. 8

CARDIAC HARNESS HAVING AN OPTIMAL IMPEDANCE RANGE

BACKGROUND OF THE INVENTION

1. Field of the Invention

The present invention relates to a device for treating heart failure. More specifically, the invention relates to a cardiac harness having electrodes for providing defibrillation and/or pacing/sensing therapies. The design of the cardiac harness provides electrodes integrated with the cardiac harness having an impedance that optimize the compatibility of the system with commercially available internal cardioverter defibrillators.

2. General Background and State of the Art

Cardiac harnesses, such as those disclosed in U.S. Ser. No. 10/704,376 ("the '376 application"), may be used to treat cardiac heart failure. The entire contents of the '376 application is incorporated herein by reference. To treat other heart failures, including cardiac arrhythmias, the cardiac harness of the '376 application may include electrodes that are connected to an implantable cardioverter defibrillator ("ICD"), which are well known in the art. Such electrodes are capable of delivering a defibrillating electrical shock from the ICD to the heart. These electrodes may also provide pacing/sensing functions to the heart to treat cardiac failures, including bradycardia and tachycardia.

It is desirable to have the cardiac harness with electrodes be compatible with commercially available ICDs and defibrillation capable cardiac resynchronization therapy ("CRT-D") and pulse generators ("PG"), such as those from Guidant, Medtronic, and St. Jude Medical. In order to be compatible with these commercially available ICDs and CRT-D PGs the electrodes of the cardiac harness must have an appropriate electrical impedance. If the system (cardiac harness with electrodes connected to a power source) has an impedance that is too low, the system could become damaged. On the other hand, if the system has an impedance that is too high, the system may produce an insufficient amount of electric current to travel across the cardiac tissue to sufficiently depolarize a critical amount of cardiac tissue to result in termination of the fibrillating wavefronts. Therefore, what is needed is a cardiac harness having defibrillation and/or pacing/sensing capabilities, wherein the electrodes of the cardiac harness have an impedance that is within an appropriate range.

SUMMARY OF THE INVENTION

In accordance with the present invention, a system for treating the heart includes a cardiac harness configured to conform generally to at least a portion of a patient's heart. The system also includes at least one electrode associated with the cardiac harness and positioned proximate to an outer surface of the heart, and a power source in communication with the electrode. The electrode and power source are at least a part of an electrical circuit. The electrical circuit may also include a conductor in communication between the electrode and the power source or the electrode and power source may communicate wirelessly. In order to ensure that the electrical circuit will function properly, the electrical circuit has an impedance between approximately 10 ohms and approximately 120 ohms. It is even more preferred that the impedance range be between approximately 20 ohms and 80 ohms. The lower impedance range is dictated by the functionality of the power source or pulse generator. Having too low of an impedance (under 10 ohms) can damage the electrical circuit incorporated with the cardiac harness. The upper impedance limit is that which continues to provide an adequate defibrillation threshold ("DFT").

Several alterations can be made to the system to increase its impedance and avoid falling under the lower impedance limit of 10 ohms. In one aspect, a dielectric material such as silicone rubber is disposed on a pericardial side of the electrode (side of electrode facing away from the heart), leaving an epicardial side of the electrode (side of electrode in contact with the heart) un-insulated. Insulating the pericardial side of the electrode increases the impedance of the system, and prevents the system from having an impedance that falls under the lower impedance limit.

In another aspect, the pitch of a normal electrode coil can be increased. Increasing the pitch of the electrode coil decreases its surface area, and consequently, increases the impedance of the system.

In yet another aspect of the present invention, the composition of the conductive wire or conductor, which may include an MP35N-Ag composite, can be altered by changing the silver content. The preferred balance of impedance and mechanical strength is achieved with a 25% silver content of the conductive wire composite. In order to keep the impedance of the present system above the lower impedance limit, the silver content within the conductor can be from 0% to about 50%.

Also, the cross-section of the wire forming the electrode can be reduced to increase the impedance. In this embodiment, changing the wire of the electrode in any way to reduce the area of its cross-section or its outer diameter will increase its impedance. The width and/or height of the cross-section of the wire forming the electrode can be reduced to decrease its cross sectional area. In another embodiment, the cross-sectional shape of the electrode coil wire may be changed to reduce its surface area. In one instance, the wire of the electrode can be changed from a rectangular cross-section to a circular cross-section.

Further, the overall outer diameter of the electrode can be reduced to increase the impedance of the system. If the electrode is in the form of a helical coil, the wire forming the coil can be wound tighter to decrease the overall outer diameter of the helical coil.

In a further aspect, a resistor can be plugged in-line with the lead system to increase the impedance of the system.

Another aspect includes an electrode with circumferentially insulating segments disposed along its length. The insulating segments can be formed of any dielectric material such as silicone rubber, and may be any size. Further, any number of insulating segments may be disposed along the electrode. The insulating segments disposed around the electrode reduce the exposed surface area of the electrode, thereby increasing the impedance. The insulating segments may also force a redistribution of current in the exposed regions of the electrode in order to optimize the DFT.

Another aspect includes an electrode with a resistive film (i.e., an oxide layer) disposed on the electrode surface. The resistive film could further be deposited non-uniformly so as to spatially modulate surface resistance (i.e., to reduce current density edge effects, or to alter the current distribution along the length of the electrode to optimize the DFT).

In yet another aspect, the length of the electrode can be shortened. By shortening the electrode, the overall surface area of the electrode is decreased, thereby increasing the impedance of the system.

BRIEF DESCRIPTION OF THE DRAWINGS

FIG. 2 is a cross-sectional view taken along line 2-2 of FIG. 1.

FIG. 3 is a partial cross-sectional view of a distal end of an electrode attached to a cardiac harness.

FIG. 4 is a cross-sectional view taken along line 4-4 of FIG. 1 showing an electrode having its pericardial side insulated.

FIG. 5 is a partial view of a helical coil of an electrode with the pitch of the winding increased.

FIG. 6a is a cross-sectional view of a wire forming an electrode with reduced dimensions.

FIG. 6b is a cross-sectional view of a wire forming an electrode with less cross-sectional area due to the change in the cross-sectional shape of the wire.

FIG. 7 is a partial view of a resistor plugged in-line with a conductor wire.

FIG. 8 is a partial view of an electrode having circumferential segments of a dielectric material disposed along the length of the electrode.

DETAILED DESCRIPTION OF THE PREFERRED EMBODIMENTS

Figure 1:
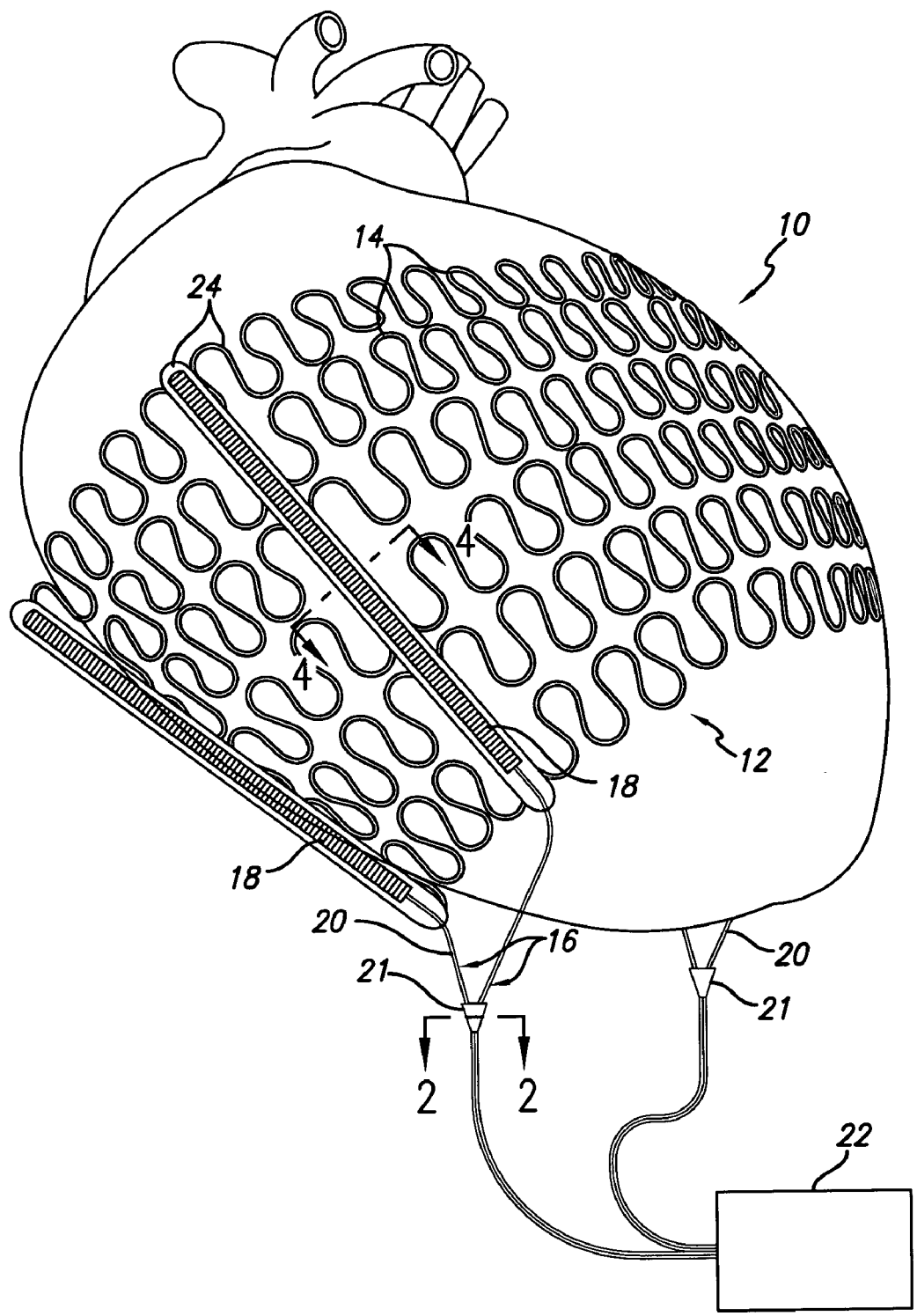
FIG. 1 is a perspective view of a cardiac harness including a lead system that is connected to a power source.

The present invention is directed to a cardiac harness system for treating the heart. The term "cardiac harness" as used herein is a device fit onto a patient's heart to apply a compressive force on the heart during at least a portion of the cardiac cycle. The cardiac harness system of the present invention couples a cardiac harness for treating the heart with a cardiac rhythm management device. More particularly, the cardiac harness includes rows or undulating strands of spring elements that provide a compressive force on the heart during diastole and systole in order to relieve wall stress pressure on the heart. Associated with the cardiac harness is a cardiac rhythm management device for treating any number of irregularities in heart beat due to, among other reasons, congestive heart failure. Thus, the cardiac rhythm management device associated with the cardiac harness can include one or more of the following: an implantable cardioverter defibrillator ("ICD") with associated leads and electrodes; a cardiac pacemaker (or cardiac resynchronization therapy ("CRT") pulse generator) including leads and electrodes used for sensing cardiac function and providing pacing stimuli to treat synchrony of both vessels; and a combined ICD and pacemaker (referred to as a ("CRT-D")), with associated leads and electrodes to provide a defibrillation shock and/or pacing/sensing functions.

The cardiac harness system may include various configurations of panels connected together to at least partially surround the heart and assist the heart during diastole and systole. The cardiac harness system also includes one or more leads having electrodes associated with the cardiac harness and a source of electrical energy supplied to the electrodes for delivering a defibrillating shock or pacing stimuli.

In one embodiment of the invention, as shown in FIG. 1, a cardiac harness 10 includes four panels 12 of generally continuous undulating strands 14. A panel includes rows or undulating strands of hinges or spring elements that are connected together and that are positioned between a pair of electrodes, the rows or undulations being highly elastic in the circumferential direction and, to a lesser extent, in the longitudinal direction. The cardiac harness also includes separate leads 16 having conductive electrode portions 18 that are spaced apart and which separate the panels 12. As shown in FIG. 1, the electrodes are formed of a conductive coil wire, preferably in a helical manner. A conductive wire or conductor 20 is attached to the coil wire and to a power source 22, forming a part of the electrical circuitry of the system. As used herein, the power source can include any of the following, depending upon the particular application of the electrode: a pulse generator ("PG"); an ICD; a pacemaker or CRT; and an implantable cardioverter defibrillator coupled with a pacemaker or CRT-D. In the embodiment shown in FIG. 1, the electrodes are configured to deliver an electrical shock, via the conductive wire and the power source, to the epicardial surface of the heart so that the electrical shock passes through the myocardium. The electrodes can be spaced so that they are about 0° apart, 45° apart, 60° apart, 90° apart, 120° apart, or any arbitrary arc length spacing, or, for that matter, essentially any arc length apart around the circumference of the heart in order to deliver an appropriate electrical shock. As previously described, it may become necessary to defibrillate the heart and the electrodes 18 are configured to deliver an appropriate electrical shock to defibrillate the heart.

In the embodiment shown in FIG. 1, a Y-junction member 21 is used to join two adjacent conductor wires 20. As best shown in FIG. 2, the Y-junction is a low-profile molding of silicone rubber or other dielectric material having two lumens 23, one for each conductor wire. Any number of lumens may be formed within the Y-junction to join more than 2 conductor wires. In this embodiment, the proximal ends of the joined conductors are crimped together into a pin (not shown) that is attached to the power source 22. The molding that forms the Y-junction member may extend from the Y-junction to the power source, or may only extend a certain distance that ends before the power source. The Y-junctions helps to organize and manage the conductors within a patient's body. In other embodiments, the conductors may not be joined together with the Y-junction member.

As best shown in FIG. 3, the electrodes 18 are attached to the cardiac harness 10, and more particularly to the undulating strands 14, by a dielectric material 24. The dielectric material insulates the electrodes from the cardiac harness so that electrical current does not pass from the electrode to the harness thereby undesirably shunting current away from the heart for defibrillation. Preferably, the dielectric material covers the undulating strands and covers at least a portion of the electrodes 18. FIG. 3 also shows in more detail how the conductive wire or conductor 20 is in communication with the electrode 18. In the embodiment shown, the electrode portion is a ribbon of conductive material that is coiled around and welded to a dome 26 at a distal end of the cardiac harness. The dome is also formed of a conductive material (such as MP35N) and has a distal end with a blind hole 28, and a proximal end forming a seat 30. During manufacturing, silicone rubber or another dielectric material flows into the blind hole 28 to help attach the dielectric material at the end of the electrode. Also during assembly, a distal end of the conductor wire 20 is placed and crimped within the seat 30, thereby placing the conductor in electrical communication with the electrode 18 via the dome 26. In this embodiment, the contact junction between the conductor and the electrode is at the distal end of the cardiac harness where there is less bending moments, and therefore, it is less likely that this contact junction will fracture or fatigue. FIG. 3 shows the dielectric material 24 molded around the ends of the undulating strands 14, and a cap 32 disposed at the end of the undulating strand. Grip pads (not shown) may also be attached to the dielectric material to help hold the cardiac harness in place once positioned around a potion of a beating heart.

The cardiac harness 10 may be produced in a range of sizes, with distinct lengths depending on the size and the number or rows of undulating strands 14. In the embodiment shown in FIG. 1, the cardiac harness includes six rows of undulating strands, however, other embodiments may include fewer or more rows of undulating strands. The electrode 18 length and surface area is preferably proportional with the harness length. For example, the length and surface area of the electrode can be approximately 49 mm and 307 mm$^2$, 65 mm and 407 mm$^2$, and 81 mm and 505 mm$^2$ for a cardiac harnesses having four, five, and six undulating strand rows, respectively. However, the size of the electrode may remain constant regardless of the size of the cardiac harness.

In one embodiment, the cardiac harness 10 is intended to function with commercially available pace/sense leads and ICD pulse generators. To ensure the cardiac harness is compatible with commercially available ICD and CRT-D pulse generators, it must have an appropriate electrical impedance. Commercially available ICD and CRT-D pulse generators, such as those from Guidant, Medtronic, and St. Jude Medical, typically have a lower impedance limit below which the device will not deliver a shock during programmed device testing at implantation. This limit, typically 20Ω, is dictated by the current carrying limits of the internal pulse generator circuitry. Since the ICD delivers a set voltage from a charged capacitor, as the system impedance drops, the delivered current increases. Once implanted, the ICD should deliver a defibrillation shock even if the impedance drops below 20Ω, although there is a risk that the circuitry of the system will be damaged. Depending on the initial voltage, actual unit range of the lead system attached to the cardiac harness is no lower than about 20Ω, with a functional limit of about 10Ω.

Several parameters affect the system impedance. These include, but are not limited to, the inherent resistivity of the tissue volume through which the defibrillation current flows (may be affected by tissue density, tissue fluid levels, air volume, etc.); the distance between the electrodes attached to the cardiac harness; the surface area of the electrodes exposed to the body tissues; the electrode geometry (and impact on current edge effects); the inter-relationship between isopotential lines of current flow; the resistance in the lead electrodes, conductors, and contact junctions, and ICD or CRT-D circuitry; electrode material (polarization effects) and microscopic surface texture (i.e., fractal coatings, black Pt, etc.); and the morphology of the shock waveform (i.e., repolarization effects of a biphasic waveform).

As the length of the electrode 18 increases to extend along cardiac harnesses of varying lengths, the impedance of the system decreases. In other words, the larger cardiac harness have longer electrodes with more exposed surface area than the electrodes attached to smaller cardiac harnesses, and the electrical circuitry associated with the longer electrodes also have a lower impedance than the electrical circuitry associated with the smaller electrodes. Therefore, what is needed is a way to increase the impedance of the system to avoid falling under the lower impedance limit of 20Ω. In one embodiment as shown in the cross-sectional view of FIG. 4, dielectric material such as silicone rubber 34 is disposed on a pericardial side 36 (side of electrode facing away from the heart) of the electrode, leaving an epicardial side 38 (side of electrode in contact with the heart) of the electrode un-insulated. Any length of the pericardial side of the electrode may be insulated up to the entire length of the electrode. Insulating the pericardial side of the electrode increases the system impedance, and thereby prevents the system from having an impedance that falls under the lower impedance limit. Although not preferred, it has also been contemplated that a certain portion of the epicardial side of the electrode could be insulated in addition to or instead of the pericardial side to reduce the electrodes surface area and increase its impedance.

In another embodiment, the pitch of electrode coil 18 can be increased. The coil shown in FIG. 5 has a greater pitch compared to the pitch of the electrode shown in FIG. 1. Increasing the pitch of the electrode coil decreases its total surface area per unit length, and consequently, increases the system impedance.

In yet another embodiment, the composition of the conductive wire or conductor 20, which may include an MP35N-Ag composite, can be altered by changing the silver content. By specifying the silver content of the conductor to be around 25%, a preferred balance of impedance and mechanical strength of the lead system is achieved. In order to keep the impedance of the present system above the lower impedance limit, the silver content within the conductor can be from 0% to about 50%.

The cross-sectional dimensions of the wire forming the electrode coil 18 can be reduced to increase the impedance. In this embodiment, changing the wire of the electrode in any way to reduce the area of its cross-section or its outer diameter will increase impedance. The width and/or height of the wire forming the electrode coil can be reduced to decrease its cross sectional area as shown in FIG. 6a, where the dotted line represents the electrode before the reduction. Also, in another embodiment as shown in FIG. 6b, the cross-sectional shape of the electrode coil wire may be changed to reduce its area. In this instance, the wire of the electrode was changed from a rectangular cross-section to a circular cross-section. In other embodiments, the cross-sectional shape may be changed to an any shape giving the electrode wire a lesser cross-sectional area, such as oval or any polygonal shape.

In other embodiments, the overall outer diameter of the electrode can be reduced to increase the impedance of the system. If the electrode is in the form of a helical coil, the wire forming the coil can be wound tighter to decrease the overall outer diameter of the helical coil, and thereby decreasing the overall surface area of the electrode.

In a further embodiment, a resistor 40 can be plugged in-line with the lead system to increase the impedance of the system. FIG. 7 is a partial view of one conductor 20, showing the resistor 40 plugged in-line with the conductor. A separate resister can be plugged in-line with each conductor of the system. The conductor 20 is usually insulated with a dielectric material 24, and as shown in FIG. 7, it is preferred that resistor also be insulated with a dielectric material.

Referring now to FIG. 8, another embodiment is shown where the electrode 18 includes circumferentially insulating segments 24 disposed along its length. Only the electrode is shown in this figure for clarity reasons, with three separate insulating segments 42 disposed completely around the electrode. The insulating segments can be formed of any dielectric material such as silicone rubber, and may be any size, up to the length of the electrode. Further, any number of insulating segments may be disposed around the electrode, including 1, 2, 3, 4, 5, etc., insulating segments. The insulating segments can also be equally spaced apart from another, or in other embodiments, can be randomly spaced apart. The insulating segments disposed around the electrode reduce the exposed surface area of the electrode, thereby increasing the impedance.

In another embodiment, the electrode 18 may include a resistive film (i.e., an oxide layer) disposed on at least a portion of its surface. The resistive film could further be deposited non-uniformly so as to spatially modulate surface resistance (i.e., to reduce current density edge effects, or to alter the current distribution along the length of the electrode to optimize the DFT). By disposing the resistive film along the surface of the electrode, the impedance of the system will increase.

In yet another embodiment, the length of the electrode 18 can be shortened. For example, the length of the electrode shown in FIG. 1 could be shortened to decrease the surface area of the electrode. By shortening the electrode, the overall surface area of the electrode is decreased, thereby increasing the impedance of the system.

The present system must also not exceed an upper impedance level. If the impedance of the system is too high, an insufficient amount of current will travel across the cardiac tissue to sufficiently depolarize a critical amount of cardiac tissue to result in termination of the fibrillating wavefronts. With biphasic waveforms, studies suggest that a voltage gradient of at least 3V/cm is required to achieve 80% defibrillation success. See Zhou X, Daubert J P, Wolf P D, Smith W M, Ideker R E; *Epicardial Mapping Of Vetricular Defibrillation With Monophasic And Biphasic Shocks In Dogs*; Circulation Research 72:145-160 (1993); which is hereby incorporated by reference. So, while there is no particular upper impedance limit, the impedance needs to be within a reasonable range to ensure defibrillation success. One way to define a reasonable upper limit is to first determine what impedance values are typical in commercially available devices that have acceptable DFT values.

The typical system shock impedance values seen in humans have been reported in various studies (see table shown in Appendix 1). The data from the table of Appendix 1 was gathered from the following references, also listed in Appendix 1; 1) Rinaldi A. C., Simon R. D., Geelen P., Reek S., Baszko A., Kuehl M., Gill J. S., *A Randomized Prospective Study Of Single Coil Versus Dual Coil Defibrillation In Patients With Ventricular Arrhythmias Undergoing Implantable Cardioverter Defibrillator Therapy*, Journal of Pacing and Clinical Electrophysiology 26:1684-1690 (2003); 2) Gold M R, Olsovsky M R, Pelini M A, Peters R W, Shorofsky S R, *Comparison Of Single And Dual Coil Active Pectoral Defibrillation Lead Systems*, Journal of the American College of Cardiology 1391-4 (1998); 3) Schulte B, Sperzel J, Carlsson J, Schwarz T, Ehrlich W, Pitschner H F, Neuzner J, *Dual-Coil Vs. Single-Coil Active Pectoral Implantable Defibrillator Lead Systems: Defibrillation Energy Requirements And Probability Of Defibrillation Success At Multiples Of The Defibrillation Energy Requirements*, Europace 3:177-180 (2001); 4) Sandstedt B, Kennergren C, Edvardsson N, *Bidirectional Defibrillation Using Implantable Defibrillators: A Prospective Randomized Comparison Between Pectoral And Abdominal Active Generators*, Journal of the American College of Cardiology 1343-1353 (2001); and 5) Shorofsky S R, Peters R W, Rashba E J, Gold M R, *Comparison Of Step-Down And Binary Search Algorithms For Determination Of Defibrillation Threshold In Humans*, Journal of Pacing and Clinical Electrophysiology 27:218-220 (2004). All of these references are herein incorporated by reference.

Based on the data from the above references, the mean impedance at implant for a dual coil active pectoral PG system is about 40Ω (standard deviation ranges 4-10Ω), and about 60Ω±10Ω for a single coil active PG system. The single (distal) coil used in these studies was about 50 mm long and had a surface area of about 450-480 mm$^2$. The second (proximal) coil in the dual-coil systems was about 72 mm long and had a surface area of about 660-671 mm$^2$.

To compare, a study in pigs was conducted to determine the DFT at the time of implantation of one embodiment of a cardiac harness having four rows of undulating strands and with 60° intra-electrode spacing. The electrodes incorporated with the cardiac harness used in this experiment had an exposed inner and outer coil surface with a surface area of about 660 mm$^2$. The results from this study are presented in U.S. Ser. No. 11/051,823 ("the '823 application"), which is hereby incorporated by reference in its entirety. In one experiment, the a defibrillation vector for the defibrillating cardiac harness system was created from the right ventricular electrodes of the cardiac harness to the left ventricular electrodes of the cardiac harness and the active can coupled together. For this experiment, as listed in the '823 application, the mean DFT was 9.6 J and the impedance was measured at 27Ω. Also listed in the '823 application were comparable values for the mean DFT and impedance from a standard single lead defibrillation coil in the right ventricular endocardium, with a defibrillation vector from the defibrillation coil to the active can. The mean DFT was determined to be 19.3 J and the impedance was measured at 46Ω. Compared with the human data from a similar system reported in Appendix 1, the mean DFT values of the pig experiment with the defibrillation vector from the defibrillation coil disposed in the right ventricular endocardium to the active can are about 8 J higher and the impedance slightly lower. Also of note in the pig study was the advantage of increasing the intra-pair electrode spacing in lowering the mean DFT.

As with other commercially available epicardial patches and, to some extent, endocardial leads, it is anticipated that the impedance of the implant will change with time after implantation. See Schwartzman D, Hull M L, Callans D J, Gottlieb C D, Marchlinski F E; *Serial Defibrillation Lead Impedance In Patients With Epicardial And Nonthoracotomy Lead Systems*; Journal of Cardiovascular Electrophysiology 7:697-703 (1996), which is hereby incorporated by reference. Thus, when designing the cardiac harness implant to function with an ICD or CRT-D system, consideration of the time course of impedance change is important to ensure the system remains functional throughout the healing phase.

In order to test a cardiac harness having six-rows of undulating strands, additional bench-top tests were conducted in a saline tank with the cardiac harness including defibrillation electrodes placed over a saturated heart-shaped piece of foam (to mimic a human heart). Shock tests on a cardiac harness including defibrillation electrodes, which were exposed or un-insulated on both sides of the electrode, and having four-rows of undulating strands were performed. The defibrillation vector of this test simulated the vector from the right ventricular pair of electrodes to the left ventricular pair of electrodes coupled to the active can in the left pectoral region. During this test, the impedance was measured at about 26Ω (similar to the pig data referenced above). Repeating the test with the six-row cardiac harness including defibrillation electrodes with 600 intra-electrode spacing, and inner and outer coil surface exposed giving an electrode surface area of about 1060 mm$^2$ per pair, resulted in an impedance of about 20Ω, which is less than the impedance of the smaller cardiac harness.

Because of the concern that the six-row cardiac harness including defibrillation electrodes would have an impedance too close to the lower limit of the ICD, the design of the cardiac harness was altered by adding silicone rubber insulation to the outside (pericardial side) of the electrodes, leaving only the inside surface (or epicardial side) exposed. This resulted in an exposed electrode surface area of the four-row and six-row pairs of 330 mm$^2$ and 530 mm$^2$, respectively. The expectation was that by reducing the electrode surface area, the impedance would increase. A repeat of the above in-vitro tests resulted in the four-row cardiac harness having its impedance increase from about 26Ω to about 39Ω, and the six-row cardiac harness having its impedance increase from about 20Ω to about 30Ω. A comparison of 60° and 45° intra electrode separation showed no significant difference in the impedance level.

While insulating the outside of the electrode was one way to increase impedance, other methods, such as those discussed above can also be used to increase or otherwise modify the system shock impedance.

Again, the lower impedance range is dictated by the functionality of the power source or pulse generator. This is preferably no lower than about 20Ω, with a functional limit of about 10Ω. The upper impedance limit is that which continues to provide an adequate DFT. Given the data in humans discussed above, the preferred upper impedance range is about 80Ω. However, as noted in the pig study, the cardiac harness with defibrillating electrode geometry may provide a more uniform distribution of current compared to commercial leads, and therefore may be able to provide adequate voltage gradients with higher impedance values than are reported with conventional electrodes. Thus, the functional impedance range is estimated to run about 50% higher, up to 120Ω. In summary, the preferred impedance range for the cardiac harness with lead system is about 20Ω to about 80Ω, with a functional range of about 10Ω to 120Ω.

Although the present invention has been described in terms of certain preferred embodiments, other embodiments that are apparent to those of ordinary skill in the art are also within the scope of the invention. Accordingly, the scope of the invention is intended to be defined only by reference to the appended claims. While the impedance values, electrode dimensions, types of materials and coatings described herein are intended to define the parameters of the invention, they are by no means limiting and are exemplary embodiments.

APPENDIX 1

DFT and Impedance Literature References for Commercially Available Electrodes

| Ref | Study Type | Mfr | Lead System | PG Location, [A]ctive or [P]assive | Impedance (Ω) Vector 1 | Impedance (Ω) Vector 2 | DFT (J) Vector 1 | DFT (J) Vector 2 | # Pts Studied | Patient Characteristics |
|-----|-----------|-----|-------------|-----|---------|---------|---------|---------|---------|---------|
| 1 | Dual vs. Single Coil ICD | GDT | Endotak Reliance (dual) and Reliance S (single) with Ventak Prizm and Ventak Mini | Pectoral [A] | RV→SVC + Can 41 ± 5 | RV→Can 63 ± 10 | RV→SVC + Can 10.2 ± 5.2 | RV→Can 10.3 ± 4.1 | 38 dual 38 single | 60% Ischemic Mean LVEF = 40.6% VT in 52.6%; VF in 38.4% 34-39% on amio; 5-8% on sotalol Procedure Time (min): 93 ± 44 dual 86 ± 33 single |
| 2 | Dual vs. Single Coil ICD | GDT | Endotak DSP with emulator and external defibrillator; Prox coil disconnected for single config. | Pectoral [A] | RV→SVC + Can 39 ± 7 | RV→Can 57 ± 11 | RV→SVC + Can 8.7 ± 4 | RV→Can 10.1 ± 5 | 25 dual 25 single | 70% Ischemic Mean LVEF = 31 ± 13% 8% pts on amio |
| 3 | Dual vs. Single Coil ICD | GDT MDT | GDT Endotak (dual) and MDT Sprint (single) with Ventak PG (MDT PG used in 7/80) | Pectoral [A] | RV→SVC + Can 39.8 ± 4.2 | RV→Can 50 ± 5.8 | RV→SVC + Can 8.0 ± 3.6 | RV→Can 8.4 ± 3.7 | 40 dual 40 single | 48-55% Ischemic LVEF = 29.3-31.3 ± 12% 23-25% pts on amio |
| 4 | Abdominal vs. Pectoral Active Can ICD with Dual Coil Leads | SJM | SPL dual coil with Ventritex Contour emulator | Pectoral [A] Abdominal [A] | RV→SVC + Can-pect 43.8 ± 3.4 | RV→SVC + Can-abd 40.8 ± 3.3 | RV→SVC + Can-pect 9.7 ± 5.2 | RV→SVC + Can-abd 10.9 ± 5.1 | 25 pect 25 abd (same) | 60% Ischemic LVEF = 44 ± 12% 8% amio; 24% sotalol Procedure Times (min): Skin—Skin 114 ± 23 (range 79-180) Anesthesia time 167 ± 31 min (range 130-240) |

APPENDIX 1-continued

DFT and Impedance Literature References for Commercially Available Electrodes

| Ref | Study Type | Mfr | Lead System | PG Location, [A]ctive or [P]assive | Impedance (Ω) Vector 1 | Impedance (Ω) Vector 2 | DFT (J) Vector 1 | DFT (J) Vector 2 | # Pts Studied | Patient Characteristics |
|---|---|---|---|---|---|---|---|---|---|---|
| 5 | Step-down vs. Binary Search DFT protocol | MDT | MDT dual coil with active PG | Pectoral [A] | RV→SVC + Can-pect Step down 42 ± 10 | RV→SVC + Can-pect Binary 42 ± 11 | RV→SVC + Can-pect Step down 8.1 ± 0.7 | RV→SVC + Can-pect Binary 8.2 ± 5.0 | 44 Step 44 Binary (same) | 62% CAD LVEF = 33 ± 13% 14% amio; 5% sotalol |

Appendix 1
1) Rinaldi A C, Simon R D, Geelen P, Reek S, Baszko A, Kuehl M, Gill J S, A Randomized Prospective Study Of Single Coil Versus Dual Coil Defibrillation In Patients With Ventricular Arrhythmias Undergoing Implantable Cardioverter Defibrillator Therapy, Journal of Pacing and Clinical Electrophysiology 26: 1684-1690 (2003);

2) Gold M R, Olsovsky M R, Pelini M A, Peters R W, Shorofsky S R, Comparison Of Single And Dual Coil Active Pectoral Defibrillation Lead Systems, Journal Of The American College Of Cardiology: 1391-4 (1998);

3) Schulte B, Sperzel J, Carlsson J, Schwarz T, Ehrlich W, Pitschner H F, Neuzner J, Dual-Coil Vs. Single-Coil Active Pectoral Implantable Defibrillator Lead Systems: Defibrillation Energy Requirements And Probability Of Defibrillation Success At Multiples Of The Defibrillation Energy Requirements, Europace 3: 177-180 (2001);

4) Sandstedt B, Kennergren C, Edvardsson N, Bidirectional Defibrillation Using Implantable Defibrillators: A Prospective Randomized Comparison Between Pectoral And Abdominal Active Generators, Journal Of The American College Of Cardiology: 24: 1343-1353 (2001); and 5) Shorofsky S R, Peters R W, Rashba E J, Gold M R, Comparison Of Step-Down And Binary Search Algorithms For Determination Of Defibrillation Threshold In Humans, Journal of Pacing and Clinical Electrophysiology 27: 218–220 (2004).

We claim:

1. A system for treating the heart, comprising:
   a cardiac harness configured to conform generally to and apply a compressive force to at least a portion of a patient's heart;
   an electrode attached to the cardiac harness and positioned on or proximate to the epicardial surface of the heart;
   a power source in communication with the electrode, the electrode and power source are at least a part of an electrical circuit; and
   the electrical circuit having an impedance between approximately 10 ohms and approximately 120 ohms.

2. The system of claim 1, wherein the electrical circuit having an impedance between approximately 20 ohms and approximately 80 ohms.

3. The system of claim 1, further comprising a conductor in communication with the electrode and the power source.

4. The system of claim 3, further comprising a resistor disposed in-line with the conductor.

5. The system of claim 1, wherein the electrode includes an epicardial side opposite a pericardial side, at least a portion of the epicardial side of the electrode being insulated with a dielectric material.

6. The system of claim 1, wherein the electrode includes an epicardial side opposite a pericardial side, at least a portion of the pericardial side of the electrode being insulated with a dielectric material.

7. The system of claim 1, wherein the conductor includes less than about 50% silver.

8. The system of claim 1, wherein the electrode includes at least one segment of a dielectric material disposed circumferentially around the electrode, and the at least one segment of dielectric material has a length shorter than the length of the electrode.

9. A system for treating the heart, comprising:
   a cardiac harness configured to conform generally to and apply a compressive force to at least a portion of a patient's heart;
   an electrode associated with the cardiac harness and positioned on or proximate to the epicardial surface of the heart, the electrode having a pericardial side opposite an epicardial side;
   a power source in communication with the electrode, the electrode and power source are at least a part of an electrical circuit; and
   an insulation disposed on the pericardial side of the electrode, wherein the impedance of the electrical circuit is greater than about 10 ohms.

10. The system of claim 9, wherein the impedance of the electrical circuit is greater than about 20 ohms.

11. The system of claim 9, further comprising a conductor in communication with the electrode and the power source, wherein the conductor includes less than about 50% silver.

12. The system of claim 9, wherein the insulation is a dielectric material.

* * * * *

UNITED STATES PATENT AND TRADEMARK OFFICE
CERTIFICATE OF CORRECTION

PATENT NO. : 7,587,247 B2  Page 1 of 1
APPLICATION NO. : 11/195329
DATED : September 8, 2009
INVENTOR(S) : Schaer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 864 days.

Signed and Sealed this

Twenty-first Day of September, 2010

David J. Kappos
*Director of the United States Patent and Trademark Office*